United States Patent [19]
Ito et al.

[11] Patent Number: 5,869,525
[45] Date of Patent: Feb. 9, 1999

[54] ASCORBIC ACID DRUGS FOR INTRACEREBRAL ADMINISTRATION

[75] Inventors: Shinobu Ito, Tokyo; Eiji Ogata, Tokyo; Nobuhiko Miwa, Hiroshima, all of Japan

[73] Assignee: Showa Denko Kabushiki Kaisha, Tokyo, Japan

[21] Appl. No.: 647,767

[22] Filed: May 15, 1996

[51] Int. Cl.$^6$ .......................... A61K 31/34; A61K 31/70; A61K 31/715

[52] U.S. Cl. .............. 514/474; 514/23; 514/53; 514/54

[58] Field of Search ................ 514/23, 474, 53, 514/54

[56] References Cited

PUBLICATIONS

Yamamoto et al. Biochim Bioplays Acta (1990)1035 (1), 44–50.

Schreiber et al. Sb. Lek. (1990), 92 (2–3), 85–8 (Abstract).

Masek et al. Vopr. Pitan (1977), (6), 46–50 (Abstract).

Izquierdo et al. J. Pharm. Pharmacol. (1968), 20 (3), 210–14 (Abstract).

*Primary Examiner*—Phyllis G. Spivack
*Attorney, Agent, or Firm*—Sughrue, Mion, Zinn, Macpeak & Seas, PLLC

[57] ABSTRACT

An L-ascorbic acid drug for intracerebral administration comprising one or more stable activity L-ascorbic acid compounds and one or more blood brainbarrier deobstruents. Also disclosed is a method for increasing intracerebral concentration of L-ascorbic acid in a human being comprising administering by injection an L-ascorbic acid drug comprising one or more stable activity L-ascorbic acid compounds. Additionally disclosed is a method for increasing intracerebral concentration of L-ascorbic acid in a human being comprising administering by injection an L-ascorbic acid drug comprising one or more stable activity L-ascorbic acid compounds and one or more blood brainbarrier deobstruents. Also disclosed is a method for treating diseases or disorders that result from intracerebral bloodstream inhibition or intracerebral bloodstream lowering comprising administering by injection to a person in need of such treatment, a dosage effective amount of an L-ascorbic acid drug comprising one or more stable activity L-ascorbic acid compounds. Additionally disclosed is a method for treating diseases or disorders that result from intracerebral bloodstream inhibition or intracerebral bloodstream lowering comprising administering by injection to a person in need of such treatment, a dosage effective amount of an L-ascorbic acid drug comprising one or more stable activity L-ascorbic acid compounds and one or more blood brainbarrier deobstruents.

26 Claims, No Drawings

ASCORBIC ACID DRUGS FOR INTRACEREBRAL ADMINISTRATION

FIELD OF THE INVENTION

The present invention relates to highly active L-ascorbic acid drugs for intracerebral administration. More specifically, the present invention relates to an L-ascorbic acid drug for intracerebral administration which has good permeability through a blood brainbarrier and high intracerebral activity.

BACKGROUND OF THE INVENTION

L-ascorbic acid is an essential nutrient. It is well known that L-ascorbic acid plays an important role with respect to the encephalon, and the following literature references have reported its effectiveness against various diseases of the cranial nerve. For example, the use of L-ascorbic acid to treat schizophrenia is reported in M. Herjanic, *Orthomolecular Physiatry*, D. Hawkins and L. Pauling, ed. W. H. Freemann, San Francisco, pp. 303–315 (1973); the use of L-ascorbic acid to treat chronic alcoholism is reported in S. K. Majumder et al., "International J. Vitamin", *Nutr. Res.* 51, 274–278 (1981); the administration of L-ascorbic acid to oligophrenic children including those having Down's syndrome is reported in R. H. Harell et al, *Proc. Natl. Acad. Sci., U.S.A.*, 78:1, 574–578 (1981); the use of L-ascorbic acid to reduce the adverse reaction of L-dopa as a drug for the treatment of parkinsonism is reported in W. Sacks, G. M. Simpson, "Ascorbic Acid in Levodopa Therapy", *The Lancet*. March 1, 527, 1975; and the use of L-ascorbic acid in ameliorating depression in conjunction with adrenocorticotropic hormone therapy is reported in P. Cocchi et al, "Antidepressant Effect of Vitamin C.", *Pediatrics*, 65, 4: 862—862 (1980).

In recent years, ascorbic acid has been studied with respect to its activity as a water-soluble scavenger of intracerebral radicals which are considered to cause ischemic reperfusion disorder, a sequela of a cardiac infarction operation, angina pectoris, cerebral apoplexy and cerebral infarction. Thus, ascorbic acid is known to have a therapeutic effect on intracerebral radical disease.

Considering these effects on the brain, L-ascorbic acid has hitherto been administered to treat various conditions. However, when administered perorally or by phleboclysis, due to the presence of the blood brainbarrier, L-ascorbic acid in the blood may fail to reach the cerebral cells in a sufficient amount, and the desired effect on the brain by administering L-ascorbic acid cannot be satisfactorily achieved.

SUMMARY OF THE INVENTION

An object of the present invention is to provide an L-ascorbic acid drug for intracerebral administration, which drug is capable of retaining the activity of L-ascorbic acid in vivo for a long period of time and is capable of passing through the blood brainbarrier, to thereby increase the ascorbic acid concentration in cerebral cells and enhance the therapeutic effect of L-ascorbic acid.

The present inventors have conducted extensive investigations on the formulation of an L-ascorbic acid drug for intracerebral administration so that its stability in vivo is maintained and so that the L-ascorbic acid can pass through the blood brainbarrier. As a result, the present inventors have found that a drug for intracerebral administration comprising a stable activity-type L-ascorbic acid and a blood brainbarrier deobstruent provides, upon administration by phleboclysis, an increase in the therapeutic effects of L-ascorbic acid on the brain to thereby achieve the present invention. More specifically, the present invention relates to an L-ascorbic acid drug for intracerebral administration comprising a combination of an L-ascorbic acid source compound selected from stable activity type L-ascorbic acids and a compound selected from blood brain barrier deobstruents.

In another embodiment, the present invention relates to a method for increasing intracerebral concentration of L-ascorbic acid in a human being comprising administering by injection an L-ascorbic acid drug comprising one or more stable activity-type L-ascorbic acid compounds.

In yet another embodiment, the present invention relates to a method for increasing intracerebral concentration of L-ascorbic acid in a human being comprising administering by injection an L-ascorbic acid drug comprising one or more stable activity-type L-ascorbic acid compounds and one or more blood brainbarrier deobstruents.

In yet another embodiment, the present invention relates to a method for treating diseases or disorders that result from intracerebral bloodstream inhibition or intracerebral bloodstream lowering comprising administering by injection to a person in need of such treatment a dosage effective amount of an L-ascorbic acid drug comprising one or more stable activity-type L-ascorbic acid compounds.

In yet another embodiment, the present invention relates to a method for treating diseases or disorders that result from intracerebral bloodstream inhibition or intracerebral bloodstream lowering comprising administering by injection to a person in need of such treatment a dosage effective amount of an L-ascorbic acid drug comprising one or more stable activity-type L-ascorbic acid compounds and one or more blood brainbarrier deobstruents.

DETAILED DESCRIPTION OF THE INVENTION

The present invention is described in detail below.

The stable activity-type L-ascorbic acid of the present invention is an L-ascorbic acid derivative which is physically stable due to its higher resistance to oxidation as compared to L-ascorbic acid. Furthermore, the stable activity-type L-ascorbic acid readily hydrolyzes in vivo into L-ascorbic acid to exhibit bioactivity, and has a solubility in water or blood of 1 $\mu$M or more, preferably 0.001 mM or more.

Examples of the stable activity-type L-ascorbic acid for use in the present invention include an L-ascorbic acid-2-monophosphoric ester and salts thereof such as L-ascorbic acid-2-monophosphate (sometimes called L-ascorbic acid-2-monophosphoric ester), sodium L-ascorbic acid-2-monophosphate, potassium L-ascorbic acid-2-monophosphate, magnesium L-ascorbic acid-2-monophosphate, calcium L-ascorbic acid-2-monophosphate, aluminum L-ascorbic acid-2-monophosphate, and an L-ascorbic acid-2-glucoside. Two or more of these may be used in combination. Among the stable activity-type L-ascorbic acids, in view of high physical stability and relatively low price, L-ascorbic acid-2-monophosphoric ester and salts thereof and an L-ascorbic acid 2-glucoside are preferred. L-ascorbic acid-2-monophosphoric ester and the sodium salt, potassium salt and magnesium salt thereof and L-ascorbic acid 2-glucoside are more preferred.

With respect to the stable activity-type L-ascorbic acids for use in the present invention, particularly, L-ascorbic acid-2-monophosphoric ester and salts thereof such as L-ascorbic acid-2-monophosphate, sodium L-ascorbic acid-2-monophosphate, potassium L-ascorbic acid-2-monophosphate, magnesium L-ascorbic acid-2-monophosphate, calcium L-ascorbic acid-2-monophosphate and aluminum L-ascorbic acid-2-monophosphate, the production method, purification method and addition thereof to cosmetics or feeds is described, for example, in Japanese Unexamined Patent Publication Nos. 63-273489, 63-214190, 01-199590 (production method), 59-51293 (purification method), 62-285759, 62-198615, 62-175142, 62-96410, 63-267709 and 63-243014 (addition to cosmetics or feeds). The production method of L-ascorbic acid-2-glucoside is described in Japanese Unexamined Patent Publication Nos. 03-135992 and 03-139288. The stable activity-type L-ascorbic acids described in these patent publications can be used in the injection preparation of the present invention.

Sodium L-ascorbic acid-2-monophosphoric ester and magnesium L-ascorbic acid-2-monophosphoric ester are currently produced on an industrial scale and are commercially available from Showa Denko KK. L-ascorbic acid-2-glucoside is industrially produced by and commercially available from Rin'gen Seibutsu Kagaku Kenkyusho (Rin'gen Biochemical Institute). These commercially available stable activity-type L-ascorbic acids may be used in the injection preparation of the present invention.

The stable activity-type L-ascorbic acid of the present invention for administration by injection (for example, by intracerebral injection or by phleboclysis in such manner that the drug enters the brain) in combination with a blood brainbarrier deobstruent is administered to a human being in a dose of from 0.01 to 100 μmol per kg of body weight. When the blood brainbarrier deobstruent is selected from saccharides, the deobstruent is administered to a human being in a dose of from 10 to 1,000 μmol per kg of body weight, and when the blood brainbarrier deobstruent is selected from those other than saccharides, the deobstruent is administered to a human being in a dose of from 0.001 to 10 μmol per kg of body weight. The inventive L-ascorbic acid drug is administered at a frequency of from 1 to 4 times within a 24 hour period.

The stable activity-type L-ascorbic acid for administration by injection (no blood brainbarrier deobstruent) to thereby increase the intracerebral concentration of L-ascorbic acid is administered to a human being in a dose of from 0.1 to 1,000 μmol per kg of body weight at a frequency of from 1 to 4 times within a 24 hour period.

The concentration of the stable activity-type L-ascorbic acid that is compounded into an injection preparation of the present invention is from 0.001 to 10,000 mM, preferably from 0.001 to 100 mM, more preferably from 0.001 to 1 mM, based on the total solution weight.

The concentration of the blood brainbarrier deobstruent for compounding into the drug for intracerebral administration of the present invention is suitably selected depending on the concentration of the stable activity-type L-ascorbic acid to be mixed therewith, the form of the drug and method for intracerebral administration, and the kind of blood brainstem deobstruent. For example, when the drug for intracerebral administration is in the form of an injection solution and the blood brainstem deobstruent is a saccharide, the saccharide is preferably compounded into the preparation (injection solution) in a concentration of from 0.01 to 50 wt % based on the entire weight of the injection solution.

When the blood brainbarrier deobstruent is selected from materials other than saccharides and when the drug for intracerebral administration is in the form of an injection solution, the deobstruent is preferably compounded into the preparation of the present invention at a concentration of from 0.01 to 100 μM.

Useful blood brainbarrier deobstruents for compounding into the drug for intracerebral administration of the present invention include the saccharides described in S. I. Lapoport, Am. J. Physiol., 219: 1, 270–274 (1970), D. J. Blocks et al, J. Cereb. Blood Flow Metabol., 4: 535–545 (1984), S. I. Lapoport et al, Am. J. Physiol., 223, 2: 323–331 (1972), and E. A. Neuwelt et al, Fed. Proc., 43, 2: 214–219 (1984).

The saccharide for use as a blood brainbarrier deobstruent for compounding into the drug for intracerebral administration of the present invention may be selected from saccharides, saccharide derivatives and saccharide structural analogs. Examples of the saccharide include monosaccharides such as glucose, mannitol, galactose, fructose, xylulose, xylose and mannose; disaccharides such as lactose, xylobiose, maltose, sucrose and trehalose; polysaccharides such as galacto-oligosaccharide, fructo-oligosaccharide and dextrin; and a combination of two or more of these.

Examples of the saccharide derivative and saccharide structural analogs for use as a blood brainbarrier deobstruent of the present invention include glucuronic acid, phospho-2-D-glucuronic acid, ketogulonic acid, glycerol glycerophosphoric acid, erythorbic acid, erythorbic acid phosphate and erythorbic acid glucoside. Two or more of these may be used in combination.

Other useful blood brainstem (brainbarrier) deobstruents include those described in I. R. Stanley et al, Anals. New York Academy of Science, 481: 250–267 (1986).

Examples of the blood brainbarrier deobstruent other than the saccharides for use in the present invention include compounds such as metolazole, etoposide, cholic acids, dimethylsulfoxide and adenosine phosphates; organic acids and salts thereof such as citric acid, malic acid, phosphoric acid, edetic acid, oxalic acid, lactic acid, butyric acid, acetic acid, sialic acid and amino acids; polyhydric alcohols or water-soluble high molecular weight compounds such as propylene glycol, butylene glycol, glycerine and polyethylene glycols; and a mixture of two or more of these.

The cholic acid is selected from a bile acid, a dehydrocholic acid, a deoxycholic acid and an alkali metal salt thereof such as a sodium or potassium salt.

The adenosine phosphate is selected from adenosine phosphoric esters such as adenosine 5'-triphosphate, adenosine 5'-diphosphate and adenylic acid.

Useful blood brainbarrier deobstruents for compounding into the drug for intracerebral administration of the present invention are described, for example, in *Nippon Yakkyoku-Ho Kaisetsusho (Exposition of Japanese Pharmacopeia)*; 12th rev., Hirokawa Shoten (1991) and *Shokuhin Tenkabutsu Koteisho Kaisetsusho (Exposition of Official Writing for Food Additives)*, 6th ed., Hirokawa Shoten (1992), and the blood brainbarrier deobstruent for use in the present invention is not particularly limited if it satisfies either or both of the above-cited two regulations.

An injection preparation is preferably used in the present invention as compared to peroral administration. This is because the L-ascorbic acid can be transported into the brain most efficiently without undergoing decomposition through the digestive tract.

The injection solution preparation of the present invention may comprise an inorganic salt solution such as Ringer's solution which is used in normal injection preparations for controlling osmotic pressure.

With respect to the administration site of the injection preparation of the present invention, various injection methods may be used. Examples thereof include phleboclysis, medullary injection, intracranial injection, subarachnoid injection, endoscopic injection and intracerebral direct injection.

The drug comprising a stable activity-type L-ascorbic acid compound and a blood brainbarrier deobstruent of the present invention may be administered to treat various brain disorders. Where the brain disorder is an ischemic brain disease, the drug is administered to a human being in a daily dose of the stable activity-type L-ascorbic acid of from 0.01 to 1.00 $\mu$mol per kg of body weight. When the blood brainbarrier deobstruent is selected from saccharides, the drug of the present invention is administered to a human being such that the dose of the blood brainbarrier deobstruent is from 10 to 1,000 $\mu$mol per kg of body weight. When the blood brainbarrier deobstruent is selected from those other than saccharides, the dose of the blood brainbarrier deobstruent is from 0.01 to 10 $\mu$mol per kg of body weight. The stable activity-type L-ascorbic acid can also be administered to a human being by injection in a dose of from 1 to 500 $\mu$mol per kg of body weight (no deobstruent).

The injection preparation comprising a blood brainbarrier deobstruent is advantageous in that the dose of the stable activity-type L-ascorbic acid, which is generally expensive, is remarkably reduced to achieve a low cost preparation by using an inexpensive blood brainbarrier deobstruent such as a saccharide.

When it does not contain a blood brainbarrier deobstruent, the injection preparation of this invention is advantageous to patients suffering from diabetes or those under salt reduction treatment. This is because an excessive dosage, for example, of saccharides is not required.

The injection solution of the present invention may be produced by a known method for producing injection solutions. A typical example of the method for producing an injection solution is described below. In the case of an injection preparation for intracerebral administration, a stable activity-type L-ascorbic acid is dissolved into a sterilized, purified water for injection in a concentration, for example, of 5 $\mu$M. When mixing a blood brainbarrier deobstruent therewith, the blood brainbarrier deobstruent is dissolved in a concentration, for example, of 70 mM. The resulting solution is sterilized by filtration through a membrane filter having a pore size of 0.45 $\mu$m or less. Other than filter sterilization, sterilization may be conducted by an autoclave sterilization. However, if insoluble matter precipitates, the solution is again filtered through a membrane filter having a pore size of 0.45 $\mu$m or less. An inorganic salt such as NaCl or KCl may be added, or the solution may be diluted with a physiological salt solution so as to control the osmotic pressure thereof as needed. The solution thus obtained is subdivided into ampules, plastic bags or glass bottles in a unit size of from 10 to 1,000 ml, and then stored in a cold and dark place.

The drug for intracerebral administration of the present invention may be administered by phleboclysis, endoscopic injection administration or intracerebral direct injection. However, in view of ease in administration, phleboclysis is preferred.

When the drug for intracerebral administration of the present invention is administered by phleboclysis, the injection solution is injected into a vein such as an internal jugular vein in an amount of from 0.1 to 50 ml per kg of body weight of a human being at a velocity such that the total mass of dissolved matter is injected at a rate of 1 g/kg/hour or less. If the injection solution is in a high concentration such that the total mass of dissolved matter is 20% or more, the injection may be started with a solution in a low concentration and the concentration may be gradually increased.

The following Examples demonstrate that the injection preparation of the present invention provides remarkable effects on cerebral ischemic disorders such as cerebral disorders caused by intracerebral bloodstream inhibition or intracerebral bloodstream lowering. From these results, it is clearly seen that the drug of the present invention effectively retards the progress of cerebral diseases ascribable to bloodstream inhibition or bloodstream lowering.

Specific examples of cerebral diseases that result from intracerebral bloodstream inhibition or bloodstream lowering on which the drug of the present invention is effective include ischemic cerebral disease, ischemic reperfusion cerebral disease, hemorrhagic cerebral disease due to subarachnoid hemorrhage or arteriorrhexis, and cerebral disorders due to bloodstream lowering which results from cerebral thrombosis, cerebral apoplexy, cerebral infarction, injury or operation.

It is considered that the effects of the injection preparation of the present invention are due to an efficient increase in intracerebral concentration of L-ascorbic acid as a result of administering the preparation of the present invention.

Accordingly, the preparation of the present invention is duly expected to also provide the known effects of L-ascorbic acid on the treatment of cerebral diseases such as schizophrenia, alcoholism, Down's syndrome, parkinsonism and depression.

By simultaneously administering a stable activity-type L-ascorbic acid as an ascorbic acid source and a blood brainbarrier deobstruent, the ascorbic acid drug for intracerebral administration of the present invention provides ascorbic acid activity of long-term duration in the body and facilitates the permeation of ascorbic acid through the blood brainbarrier to increase the concentration of ascorbic acid in the cerebral cells. The clinical effect of the preparation of the present invention has been verified by experiments of its therapeutic effect on cerebral disorders due to bloodstream inhibition.

The drug of the present invention is also useful in treating vitamin C deficiency in humans.

The present invention will be described below in greater detail with reference to the following Examples and Comparative Examples, but the present invention should not be construed as being limited thereto.

EXAMPLES

A stable activity-type ascorbic acid and a blood brainbarrier deobstruent were completely dissolved in 300 ml of a sterilized Ringer's solution according to the formulations shown in Table 1 below. Then, the solutions were sterilized through a microbe elimination filter for preparing 92 injection solution Samples each in an amount of about 300 ml as the ascorbic acid drug for intracerebral administration by phleboclysis of the present invention. In the Examples, "$\mu$M" means "micromolar" and all percentages are given by weight.

TABLE 1

| Formulation No. in Samples of the Injection Solution of the Invention | Kind and Concentration of Stable Activity-Type Ascorbic Acid compounded into Ringer's Solution as the Ascorbic Acid Drug for Intracerebral Administration of the Invention | | Kind and Concentration of Blood Brainbarrier Deobstruent compounded into Ringer's Solution as the Ascorbic Acid Drug for Intracerebral Administration of the Invention |
|---|---|---|---|
| 1 | L-ascorbic acid-2-phosphate Mg salt | 40 $\mu$M | glucose, 10% |
| 2 | L-ascorbic acid-2-phosphate Mg salt | 400 $\mu$M | galactose, 10% |
| 3 | L-ascorbic acid-2-phosphate Mg salt | 4,000 $\mu$M | fructose, 10% |
| 4 | L-ascorbic acid-2-phosphate Mg salt | 40,000 $\mu$M | lactose, 10% |
| 5 | L-ascorbic acid-2-phosphate Mg salt | 40 $\mu$M | fructo-oligosaccharide, 10% |
| 6 | L-ascorbic acid-2-phosphate Mg salt | 40 $\mu$M | glucuronic acid, 10% |
| 7 | L-ascorbic acid-2-phosphate Mg salt | 40 $\mu$M | glycerol, 10% |
| 8 | L-ascorbic acid-2-phosphate Mg salt | 40 $\mu$M | arabinose, 10% |
| 9 | L-ascorbic acid-2-phosphate Mg salt | 40 $\mu$M | sucrose, 10% |
| 10 | L-ascorbic acid-2-phosphate Mg salt | 40 $\mu$M | mannitol, 10% |
| 11 | L-ascorbic acid-2-phosphate Mg salt | 40 $\mu$M | metolazole, 10 $\mu$M |
| 12 | L-ascorbic acid-2-phosphate Mg salt | 40 $\mu$M | etoposide, 5 $\mu$M |
| 13 | L-ascorbic acid-2-phosphate Mg salt | 40 $\mu$M | synthetic bile salt, 3 $\mu$M |
| 14 | L-ascorbic acid-2-phosphate Mg salt | 40 $\mu$M | sodium dehydrocholate, 5 $\mu$M |
| 15 | L-ascorbic acid-2-phosphate Mg salt | 40 $\mu$M | sodium deoxycholate, 2 $\mu$M |
| 16 | L-ascorbic acid-2-phosphate Mg salt | 40 $\mu$M | dimethylsulfoxide, 3 $\mu$M |
| 17 | L-ascorbic acid-2-phosphate Mg salt | 40 $\mu$M | adenosine 5'-triphosphate, 5 $\mu$M |
| 18 | L-ascorbic acid-2-phosphate Mg salt | 40 $\mu$M | adenosine 5'-triphosphate, 10 $\mu$M |
| 19 | L-ascorbic acid-2-phosphate Mg salt | 40 $\mu$M | adenylic acid, 5 $\mu$M |
| 20 | L-ascorbic acid-2-phosphate Na salt | 40 $\mu$M | glucose, 10% |
| 21 | L-ascorbic acid-2-phosphate Na salt | 400 $\mu$M | galactose, 10% |
| 22 | L-ascorbic acid-2-phosphate Na salt | 4,000 $\mu$M | fructose, 10% |
| 23 | L-ascorbic acid-2-phosphate Na salt | 40,000 $\mu$M | lactose, 10% |
| 24 | L-ascorbic acid-2-phosphate Na salt | 40 $\mu$M | fructo-oligosaccharide, 10% |
| 25 | L-ascorbic acid-2-phosphate Na salt | 40 $\mu$M | glucuronic acid, 10% |
| 26 | L-ascorbic acid-2-phosphate Na salt | 40 $\mu$M | glycerol, 10% |
| 27 | L-ascorbic acid-2-phosphate Na salt | 40 $\mu$M | arabinose, 10% |
| 28 | L-ascorbic acid-2-phosphate Na salt | 40 $\mu$M | sucrose, 10% |
| 29 | L-ascorbic acid-2-phosphate Na salt | 40 $\mu$M | mannitol, 30% |
| 30 | L-ascorbic acid-2-phosphate Na salt | 40 $\mu$M | metolazole, 10 $\mu$M |
| 31 | L-ascorbic acid-2-phosphate Na salt | 40 $\mu$M | etoposide, 5 $\mu$M |
| 32 | L-ascorbic acid-2-phosphate Na salt | 40 $\mu$M | synthetic bile salt, 3 $\mu$M |
| 33 | L-ascorbic acid-2-phosphate Na salt | 40 $\mu$M | sodium dehydrocholate, 5 $\mu$M |
| 34 | L-ascorbic acid-2-phosphate Na salt | 40 $\mu$M | sodium deoxycholate, 2 $\mu$M |
| 35 | L-ascorbic acid-2-phosphate Na salt | 40 $\mu$M | dimethylsulfoxide, 3 $\mu$M |
| 36 | L-ascorbic acid-2-phosphate Na salt | 40 $\mu$M | adenosine 5'-triphosphate, 20 $\mu$M |
| 37 | L-ascorbic acid-2-phosphate Na salt | 40 $\mu$M | adenosine 5'-diphosphate, 5 $\mu$M |
| 38 | L-ascorbic acid-2-phosphate Na salt | 40 $\mu$M | adenylic acid, 5 $\mu$M |
| 39 | L-ascorbic acid-2-phosphate K salt | 40 $\mu$M | glucose, 10% |
| 40 | L-ascorbic acid-2-phosphate K salt | 40 $\mu$M | glycerol, 10% |
| 41 | L-ascorbic acid-2-phosphate K salt | 40 $\mu$M | arabinose, 10% |
| 42 | L-ascorbic acid-2-phosphate K salt | 40 $\mu$M | sucrose, 10% |
| 43 | L-ascorbic acid-2-phosphate K salt | 40 $\mu$M | mannitol, 10% |
| 44 | L-ascorbic acid-2-phosphate K salt | 40 $\mu$M | sodium dehydrocholate, 5 $\mu$M |
| 45 | L-ascorbic acid-2-phosphate K salt | 40 $\mu$M | adenosine 5'-triphosphate, 5 $\mu$M |
| 68 | L-ascorbic acid-2-phosphate free acid | 40 $\mu$M | glucose, 10% |
| 69 | L-ascorbic acid-2-phosphate free acid | 40 $\mu$M | glycerol, 10% |
| 70 | L-ascorbic acid-2-phosphate free acid | 40 $\mu$M | arabinose, 10% |
| 71 | L-ascorbic acid-2-phosphate free acid | 40 $\mu$M | sucrose, 10% |
| 72 | L-ascorbic acid-2-phosphate free acid | 40 $\mu$M | mannitol, 30% |
| 73 | L-ascorbic acid-2-phosphate free acid | 40 $\mu$M | sodium dehydrocholate, 5 $\mu$M |
| 74 | L-ascorbic acid-2-phosphate free acid | 40 $\mu$M | adenosine 5'-triphosphate, 20 $\mu$M |
| 75 | L-ascorbic acid-2-glucoside | 50 $\mu$M | glucose, 10% |
| 76 | L-ascorbic acid-2-glucoside | 50 $\mu$M | glycerol, 10% |
| 77 | L-ascorbic acid-2-glucoside | 50 $\mu$M | arabinose, 10% |
| 78 | L-ascorbic acid-2-glucoside | 50 $\mu$M | sucrose, 10% |
| 79 | L-ascorbic acid-2-glucoside | 50 $\mu$M | mannitol, 30% |
| 80 | L-ascorbic acid-2-glucoside | 50 $\mu$M | sodium dehydrocholate, 5 $\mu$M |
| 81 | L-ascorbic acid-2-glucoside | 50 $\mu$M | adenosine 5'-triphosphate, 20 $\mu$M |
| 82 | L-ascorbic acid-2-glucoside | 5 mM | none |

COMPARATIVE EXAMPLE

Using the injection solutions prepared in the test segment in the Example above (Table 1) each comprising the ascorbic acid drug for intracerebral administration of the present invention and the injection solutions in the control segment shown in Table 2, the effects of the ascorbic acid drug for intracerebral administration of the present invention were compared and verified according to the following experiments.

EXPERIMENT 1:

Jirds were subjected to cerebral ischemia for 6 minutes according to a bilateral common carotid artery occlusion model, so that the concentration of hippocampal extracellular glutamine as determined by a microdialysis method was increased 11 times the concentration before ischemia. Immediately thereafter, the injection solutions according to formulation Nos. 1 to 23 in the Example of the present invention as the test segment were each injected into the internal jugular vein of a jird in an amount of 200 µl by means of an ultrafine syringe at a rate of from 4 to 8 µl/sec. Thereafter, the injection was continued once per day for 5 days. After 60 days, each of the jirds was dissected to obtain the necrosis ratio of cerebral neurocytes. The results obtained are shown in Table 3 below. As the control segment, 200 µl of each Ringer's injection solution according to the formulation in Table 2 was injected into a jird in the same manner as in the test segment. Upon viewing the jirds in the control segment by a $^{45}$Ca autoradiography/image analyzer, a slow neurocyte death, comprising necrosis of pyramidal cells in the CA1 domain (Ammon's horn) of the hippocampus in the limbic system, was observed 4 days after ischemia. Furthermore, almost all pyramidal cells necrosed 16 days after ischemia. On the other hand, injection of the ascorbic acid drug for intracerebral administration of the present invention in jirds (8 heads in one group) remarkably prevented necrosis of the neurocytes (see Table 3). The brains of jirds in the test segment and in the control segment were enucleated at the time of completion of the experiments, the ascorbic acid in the brains was extracted by homogenization with a 100-fold weight of a 1% metaphosphoric acid solution under cooling, and the amount of the ascorbic acid was measured in an ODS column by an HPLC method. As a result, the intracerebral ascorbic acid concentration in the test segment was found to be 12.7 times higher on average than that of the control segment. These results confirm that the ascorbic acid level in the brain can be remarkably elevated by administering the injection preparation of the present invention.

EXPERIMENT 2:

Jirds were each administered 200 µg/ml of methotrexate in a 10-µl intrathecal injection by means of an ultrafine syringe, and their heads were subsequently exposed to an irradiation treatment of 20-Gy rays. The treatment was continued every day for three days. Immediately after irradiation at the start of treatment, each of the injection solutions according to formulation Nos. 1 to 23 in Table 1 of the Example of the present invention as a test segment was injected into an internal jugular vein in an amount of 200 µl by means of an ultrafine syringe at a rate of from 4 to 8 µl/sec, and the injections were continued every day for 5 days. As a control segment, 200 µl of each Ringer's injection solution according to the formulations in Table 2 were injected in jirds in the same manner as in the test segment. After feeding for 60 days, the survival time of each jird was recorded and the results are shown in Table 3. Jirds in the control segment suffered from leukoencephalitis from 8 to 47 days after the initiation of treatment and died at a high proportion. Upon dissective examination, multifocal necrosis was observed in the hemicerebrum white matter. On the other hand, in jirds (10 heads in one group) injected by the ascorbic acid drug for intracerebral administration of the present invention, there was almost no death during the observation period of 60 days. Also, necrosis was not observed in jirds treated with the ascorbic acid drug for intracerebral administration of the present invention (see Table 3).

TABLE 2

| Formulation No. in Control Segment | Formulation of Injection Solution in Control Segment |
|---|---|
| 1 | 100% Ringer's injection |
| 2 | Ringer's injection containing 10% mannitol |
| 3 | Ringer's injection containing 20% mannitol |

TABLE 2-continued

| Formulation No. in Control Segment | Formulation of Injection Solution in Control Segment |
|---|---|
| 4 | Ringer's injection containing 30% mannitol |
| 5 | Ringer's injection containing 5 µM adenosine 5'-triphosphate |
| 6 | Ringer's injection containing 10 µM adenosine 5'-triphosphate |
| 7 | Ringer's injection containing 20 µM adenosine 5'-triphosphate |
| 8 | Ringer's injection containing 40 µM L-ascorbic acid-2-phosphate Mg salt |
| 9 | Ringer's injection containing 40 µM L-ascorbic acid-2-phosphate Na salt |
| 10 | Ringer's injection containing 40 µM L-ascorbic acid |
| 11 | Ringer's injection containing 40 µM L-ascorbic acid-2-glucoside |
| 12 | Ringer's injection containing 40 µM L-ascorbic acid-2-phosphate free acid |

TABLE 3

| Formulation No. in Table 2 in Control Segment | Necrosis Ratio of Neurocyte in Experiment 1 ($10^2$ mAU-mm$^2$) | Survival Time in Experiment 2 (days) |
|---|---|---|
| 1 | 2.3 | 21 |
| 2 | 2.5 | 25 |
| 3 | 2.4 | 22 |
| 4 | 2.5 | 25 |
| 5 | 2.4 | 20 |
| 6 | 2.3 | 26 |
| 7 | 2.2 | 25 |
| 8 | 2.2 | 22 |
| 9 | 2.3 | 26 |
| 10 | 2.6 | 26 |
| 11 | 2.7 | 22 |
| 12 | 2.5 | 26 |

| Formulation No. in Table 1 in Test Segment | Necrosis Ratio of Neurocyte in Experiment 1 ($10^2$ mAU-mm$^2$) | Survival Time in Experiment 2 (days) |
|---|---|---|
| 1 | 0.78 | 48 |
| 2 | 0.55 | 55 |
| 3 | 0.41 | 60 |
| 4 | 0.33 | 60 |
| 5 | 0.97 | 47 |
| 6 | 0.87 | 47 |
| 7 | 0.80 | 42 |
| 8 | 0.63 | 50 |
| 9 | 0.59 | 55 |
| 10 | 0.55 | 56 |
| 11 | 0.43 | 51 |
| 12 | 0.57 | 54 |
| 13 | 0.88 | 32 |
| 14 | 0.84 | 42 |
| 15 | 0.86 | 37 |
| 16 | 0.64 | 43 |
| 17 | 0.86 | 44 |
| 18 | 0.92 | 47 |
| 19 | 0.67 | 42 |
| 20 | 0.47 | 57 |
| 21 | 0.50 | 57 |
| 22 | 0.72 | 48 |
| 23 | 0.77 | 47 |

While the invention has been described in detail and with reference to specific embodiments thereof, it will be apparent to one skilled in the art that various changes and modifications can be made therein without departing from the spirit and scope thereof.

What is claimed is:

1. An L-ascorbic acid drug for intracerebral administration comprising a therapeutically effective amount for intracerebral administration of one or more stable activity L-ascorbic acid compounds and one or more blood brainbarrier deobstruents selected from the group consisting of saccharides and saccharide derivatives.

2. The drug for intracerebral administration as claimed in claim 1, wherein said stable activity L-ascorbic acid is selected from the group consisting of L-ascorbic acid-2-monophosphoric ester, and salts thereof, and an L-ascorbic acid-2-glucoside.

3. The drug for intracerebral administration as claimed in claim 1, wherein said stable activity L-ascorbic acid is selected from the group consisting of L-ascorbic acid-2-monophosphoric ester, and the sodium salt, potassium salt and magnesium salt thereof, and L-ascorbic acid 2-glucoside.

4. The drug for intracerebral administration as claimed in claim 1, comprising an injectable solution.

5. The drug for intracerebral administration as claimed in claim 4, wherein said injectable solution contains said stable activity L-ascorbic acid compound in a concentration of from 0.001 to 100 mM and said deobstruent in an amount of from 0.01 to 50 wt % based on the entire weight of the injectable solution.

6. The drug for intracerebral administration as claimed in claim 5, wherein the saccharide or saccharide derivative is selected from the group consisting of glucose, mannitol, galactose, fructose, xylulose, xylose, mannose, lactose, xylobiose, maltose, sucrose, trehalose, galacto-oligosaccharide, fructo-oligosaccharide and dextrin.

7. The drug for intracerebral administration as claimed in claim 5, wherein said saccacharide or saccharide derivative is selected from the group consisting of glucuronic acid, phospho-2-D-glucuronic acid, ketogulonic acid, glycerol glycerophosphoric acid, erythorbic acid, erythorbic acid phosphate and erythorbic acid glucoside.

8. The drug for intracerebral administration as claimed in claim 4, where the injectable solution contains said stable activity L-ascorbic acid compound in a concentration of from 0.001 to 1 mM.

9. A method for increasing intracerebral concentration of L-ascorbic acid in a human being comprising administering by intravenous injection an L-ascorbic acid drug comprising one or more stable activity L-ascorbic acid compounds.

10. The method of claim 9, comprising administering by intravenous injection an L-ascorbic acid drug comprising one or more stable activity L-ascorbic acid compounds in a dose of from 0.1 to 1,000 $\mu$mol per kg of body weight.

11. The method of claim 9, comprising administering by intravenous injection an L-ascorbic acid drug comprising one or more stable activity L-ascorbic acid compounds selected from the group consisting of L-ascorbic acid-2-monophosphoric ester and salts thereof and an L-ascorbic acid-2-glucoside in a dose of from 0.1 to 1,000 $\mu$mol per kg of body weight.

12. A method for increasing intracerebral concentration of L-ascorbic acid in a human being comprising administering by intravenous injection an L-ascorbic acid drug comprising one or more stable activity L-ascorbic acid compounds and one or more blood brainbarrier deobstruents selected from the group consisting of saccharides and saccharide derivatives.

13. The method of claim 12, comprising administering by intravenous injection an L-ascorbic acid drug comprising one or more stable activity L-ascorbic acid compounds in a dose of from 0.01 to 100 $\mu$mol per kg of body weight and one or more blood brainbarrier deobstruents selected from the group consisting of saccharides and derivatives in a dose of from 10 to 1,000 $\mu$mol per kg of body weight.

14. The method of claim 12, comprising administering by intravenous injection an L-ascorbic acid drug comprising one or more stable activity L-ascorbic acid compounds selected from the group consisting of L-ascorbic acid-2-monophosphoric ester and salts thereof and an L-ascorbic acid-2-glucoside in a dose of from 0.01 to 1.00 $\mu$mol per kg of body weight and one or more blood brainbarrier deobstruents selected from the group consisting of saccharides and saccharide derivatives.

15. The method of claim 12, comprising administering by intravenous injection an L-ascorbic acid drug comprising one or more stable activity L-ascorbic acid compounds in a dose of from 0.01 to 100 $\mu$mol per kg of body weight and one or more blood brainbarrier deobstruents selected from the group consisting of mannitol, arabinose, galactose, fructose, lactose, fructo-oligosaccharide, a glucuronic acid, glycerol, and sucrose.

16. A method for increasing intracerebral concentration of L-ascorbic acid in a human being comprising administering by phleboclysis, medullary injection, intracranial injection, subarachnoid injection, endoscopic injection or intracerebral direct injection an L-ascorbic acid drug comprising one or more stable activity L-ascorbic acid compounds and one or more blood brainbarrier deobstruents selected from the group consisting of saccharides and saccharide derivatives.

17. A method for treating cerebral diseases or disorders that result from intracerebral bloodstream inhibition comprising administering by intravenous injection to a person in need of such treatment a dosage effective amount of an L-ascorbic acid drug comprising one or more stable activity L-ascorbic acid compounds.

18. The method of claim 17, for treating ischemic cerebral disorder.

19. The method of claim 17, comprising administering by intravenous injection an L-ascorbic acid drug comprising one or more stable activity L-ascorbic acid compounds in a dose of from 1 to 500 $\mu$mol per kg of body weight.

20. The method of claim 17, comprising administering by intravenous injection an L-ascorbic acid drug comprising one or more stable activity L-ascorbic acid compounds selected from the group consisting of L-ascorbic acid-2-monophosphoric ester and salts thereof and an L-ascorbic acid-2-glucoside in a dose of from 1 to 500 $\mu$mol per kg of body weight.

21. A method for treating diseases or disorders that result from intracerebral bloodstream inhibition comprising administering by intravenous injection to a person in need of such treatment a dosage effective amount of an L-ascorbic acid drug comprising one or more stable activity L-ascorbic acid compounds and one or more blood brainbarrier deobstruents.

22. The method of claim 21 for treating ischemic cerebral disorder.

23. The method of claim 21, comprising administering by intravenous injection an L-ascorbic acid drug comprising one or more stable activity L-ascorbic acid compounds in a dose of from 0.01 to 1.00 $\mu$mol per kg of body weight and one or more blood brainbarrier deobstruents selected from the group consisting of saccharides and saccharide derivatives in a dose of from 10 to 1,000 $\mu$mol per kg of body weight.

24. The method of claim 21, comprising administering by intravenous injection an L-ascorbic acid drug comprising one or more stable activity L-ascorbic acid compounds selected from the group consisting of L-ascorbic acid-2-monophosphoric ester and salts thereof and an L-ascorbic acid-2-glucoside in a dose of from 0.01 to 1.00 $\mu$mol per kg of body weight and one or more blood brainbarrier deobstruents selected from the group consisting of saccharides and saccharide derivatives.

25. The method of claim 21, comprising administering by intravenous injection an L-ascorbic acid drug comprising one or more stable activity L-ascorbic acid compounds in a dose of from 0.01 to 1.00 μmol per kg of body weight and one or more blood brainbarrier deobstruents selected from the group consisting of mannitol, arabinose, galactose, fructose, lactose, fructo-oligosaccharide, a glucuronic acid, glycerol, and sucrose.

26. A method for treating diseases or disorders that result from intracerebral bloodstream inhibition comprising administering by phleboclysis, medullary injection intracranial injection, subarachnoid injection, endoscopic injection or intracerebral direct injection to a person in need of such treatment a dosage effective amount of an L-ascorbic acid drug comprising one or more stable activity L-ascorbic acid compounds and one or more blood brainbarrier deobstruents.

* * * * *